US00PP30591P3

(12) United States Plant Patent
Wood

(10) Patent No.: US PP30,591 P3
(45) Date of Patent: Jun. 25, 2019

(54) ***SPIRAEA* PLANT NAMED 'SMSJMLA'**

(50) Latin Name: *Spiraea japonica*
Varietal Denomination: SMSJMLA

(71) Applicant: Timothy Wood, Spring Lake, MI (US)

(72) Inventor: Timothy Wood, Spring Lake, MI (US)

(73) Assignee: Spring Meadow Nursery, Inc., Grand Haven, MI (US)

( * ) Notice: Subject to any disclaimer, the term of this patent is extended or adjusted under 35 U.S.C. 154(b) by 82 days.

(21) Appl. No.: 15/731,261

(22) Filed: May 10, 2017

(65) Prior Publication Data

US 2018/0332752 P1 Nov. 15, 2018

(51) Int. Cl.
*A01H 5/02* (2018.01)
*A01H 6/00* (2018.01)

(52) U.S. Cl.
USPC ..... Plt./226
CPC ..... *A01H 6/00* (2018.05); *A01H 5/02* (2013.01)

(58) Field of Classification Search
USPC ..... Plt./226
CPC ... A01H 5/02; A01H 5/00; A01H 5/12; A01H 6/74; A01H 6/749; A01H 6/1424
See application file for complete search history.

(56) References Cited

U.S. PATENT DOCUMENTS

2016/0183429 P1 * 6/2016 Wood ..... Plt./226

* cited by examiner

*Primary Examiner* — June Hwu
(74) *Attorney, Agent, or Firm* — Cassandra Bright

(57) ABSTRACT

A new and distinct *Spiraea* cultivar named 'SMSJMLA' is disclosed, characterized by a uniquely dwarf, dense plant habit, dark foliage and dark pink flowers. Plants have a strong flowering habit. The new variety is a *Spiraea*, normally produced as an outdoor garden or container plant.

3 Drawing Sheets

Latin name of the genus and species: *Spiraea japonica*.
Variety denomination: 'SMSJMLA'.

BACKGROUND OF THE INVENTION

The new *Spiraea* cultivar is a product of a planned breeding program conducted by the inventor, Timothy D. Wood, in Grand Haven, Mich. The objective of the breeding program was to produce new *Spiraea* varieties of compact and full habit with new and better flower and leaf colors. The breeding program resulting in this new variety began during June of 2007.

The parent varieties are unnamed, unpatented proprietary varieties of *Spiraea japonica*. Seed was bulk collected from crossing blocks of the parent varieties, and subsequently mutated. A block of 100 mature, flowering unnamed mutated seedlings, selected from crossings of the parent varieties were pretreated with 10 grays of radiation was grown out(designated M1 generation). Seed was collected from ten plants of the mutated seedlings with the best foliage and dark pink flowers. This seed grown out (M2 generation) and selected for superior foliage, flower coverage and flower color. The new variety was identified as a potentially interesting selection in 2009, at a greenhouse in Grand Haven, Mich.

Asexual reproduction of the new cultivar 'SMSJMLA' by softwood cuttings was first performed during the Summer of 2009, at commercial greenhouse in Grand Haven, Mich. Subsequent propagation has shown that the unique features of this cultivar are stable and reproduced true to type in successive generations.

SUMMARY OF THE INVENTION

The cultivar 'SMSJMLA' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SMSJMLA' These characteristics in combination distinguish 'SMSJMLA' as a new and distinct *Spiraea* cultivar:

1. Plants have a dwarf habit.
2. Plants have a uniquely tight growth habit.
3. Distinctive dark green foliage.
4. Dark pink flowers.
5. Wide, flat corymbs.

PARENT COMPARISON

As seed was bulk collected, exact parentage is unknown. It is observed however, the new variety exhibits the following differences from known *Spiraea japonica* varieties used in the breeding program:

1. Plants of the new variety are shorter and more compact.
2. Plants of the new variety have darker foliage.
3. Plants of the new variety produce corymbs which are more wider and flatter than observed in parent varieties.

COMMERCIAL COMPARISON

Plants of the new cultivar 'SMSJMLA' can be compared to the patented commercial variety *Spiraea japonica*

'Galen', U.S. Plant Pat. No. 21,712. These varieties are similar in most horticultural characteristics; however 'SMSJMLA' differs in the following:

1. The new variety is shorter than this comparator.
2. The new variety has a very tight plant habit, this comparator is more open in habit.
3. Flowers of the new variety are smaller than flower of this comparator.

BRIEF DESCRIPTION OF THE PHOTOGRAPHS

The accompanying photograph in FIG. 1 illustrates in full color a typical plant of 'SMSJMLA' grown outdoors, in Grand Haven, Mich. in a 3 gallon pot.

Figure 1:
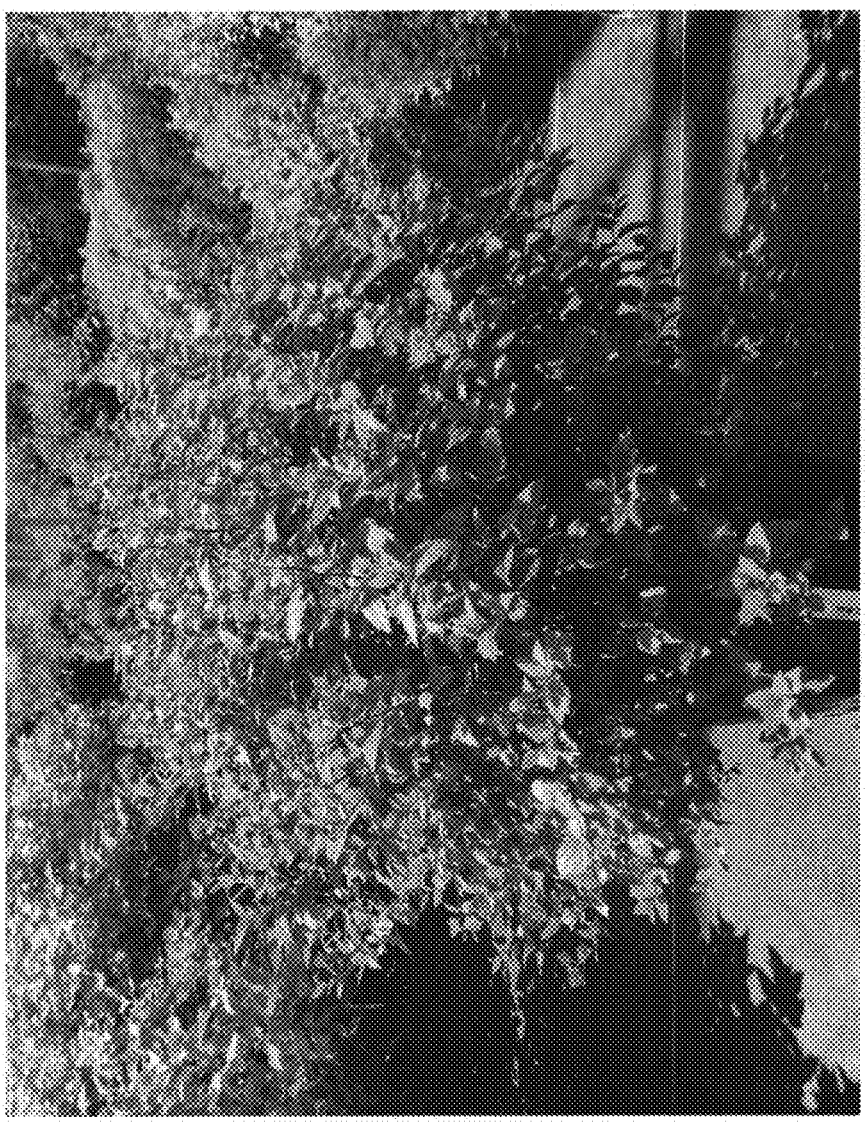
Figure 2:
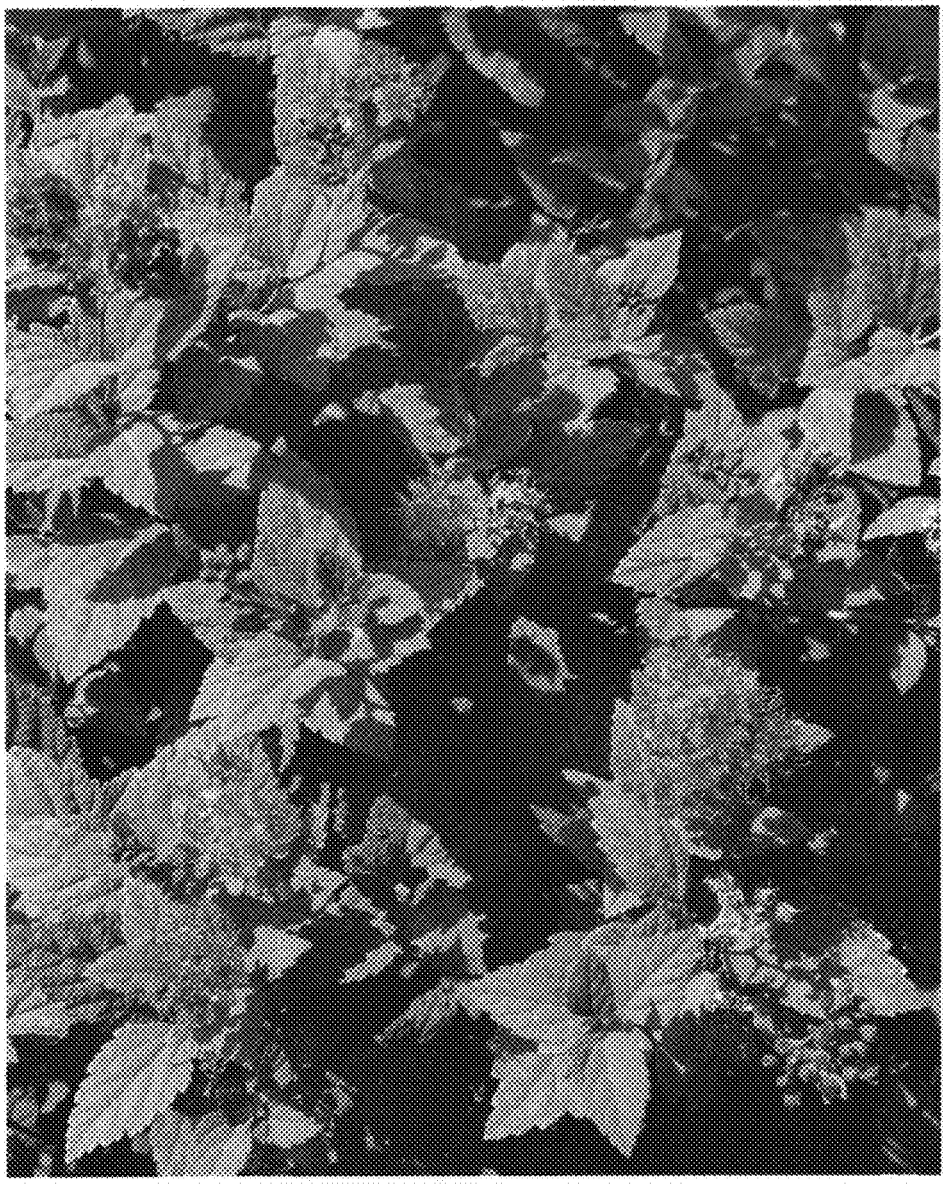
FIG. 2 illustrates a close up of mature foliage and inflorescence.
Figure 3:
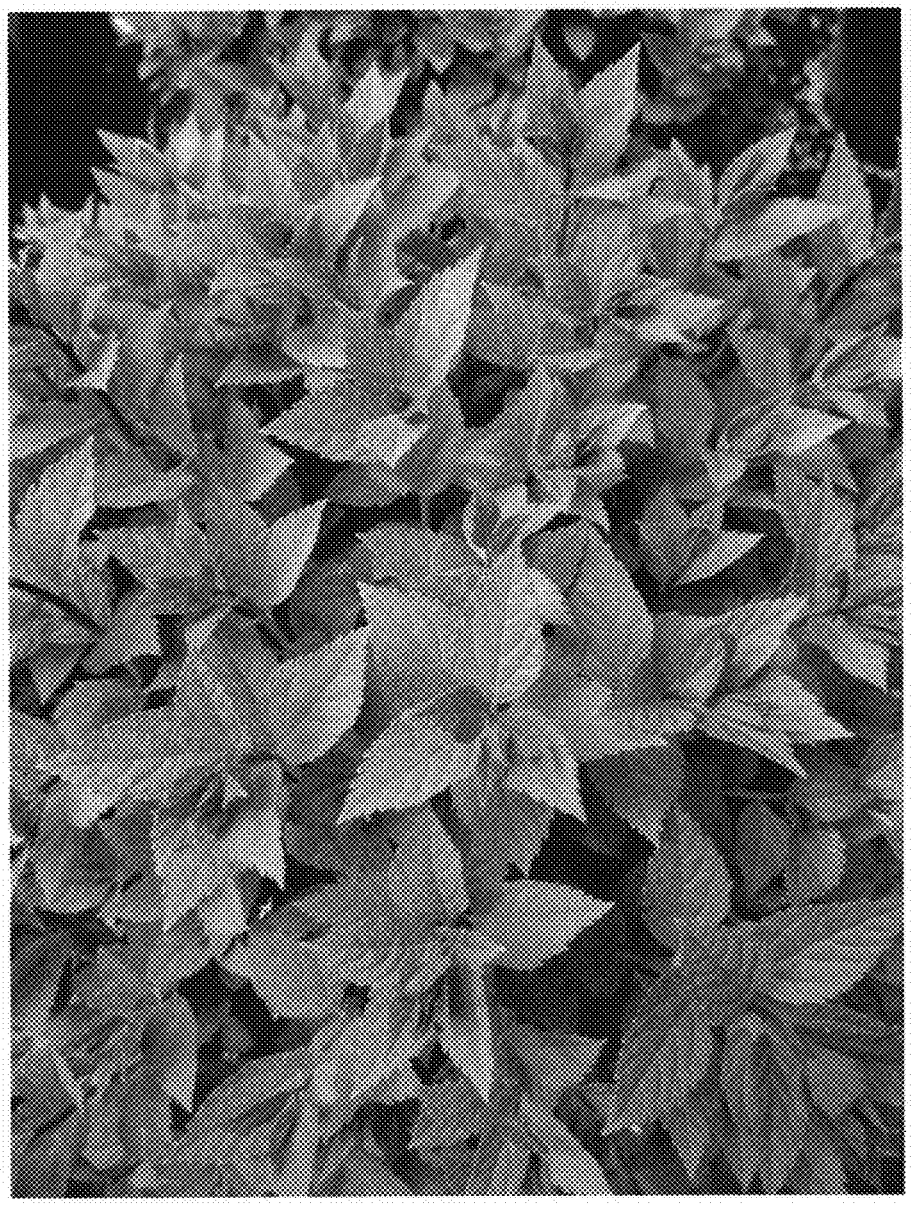
FIG. 3 illustrates in full color typical new foliage of 'SMSJMLA'. Age of the plant photographed is approximately 3 years.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 'SMSJMLA' plants grown in a commercial poly greenhouse in Grand Haven, Mich. under natural lighting. Measurements were taken during June of 2016. The plants were 2 years old in 2 gallon containers. The growing temperature ranged from 5° C. to 10° C. during the night and 18° C. to 27° C. during the day. Measurements and numerical values represent averages of typical plant types.

Botanical classification: *Spiraea japonica* 'SMSJMLA'.

Propagation:

*Time to initiate roots*.—About 15 days at approximately 22° C.

*Root description*.—Fibrous and fleshy, moderate to dense density medium thickness and freely branching. Cream to brown in color, not effectively measured with a color chart.

*Time to produce a rooted young plant*.—About 2 months at 22° C.

Plant:

*Plant type*.—Perennial shrub.

*Age of plant described*.—Approximately 2 years old.

*Growth habit*.—Dwarf shrub.

*Pot size of plant described*.—2 gallon pot.

*Overall plant shape*.—Rounded mound.

*Height*.—Approximately 36 cm.

*Plant spread*.—Approximately 49 cm.

*Growth rate*.—Fast.

*Plant vigor*.—Excellent.

*Branching characteristics*.—Basal branching, pinching required.

*Length of primary lateral branches*.—Approximately 19 cm.

*Diameter of lateral branches*.—Approximately 1.5 cm for mature growth.

*Quantity of lateral branches*.—About 26.

*Stem*.—Stem Strength: Strong. Stem Color: Near Greyed-Green 195A, bark on oldest growth near Greyed-Orange 166A. Texture: Slightly scaly. Aspect: Near straight stems held at an angle between 0-100°.

*Internode length*.—Average 1 cm.

Foliage:

*Leaf*.—Arrangement: alternate, single. Leaf shape: Ovate. Average Length: Approximately 2.5 cm. Average Width: Approximately 1.6 cm. Apex: Acute. Base: Rounded. Margin: Serrate to double serrate. Texture of top surface: Smooth, silky. Texture of bottom surface: Smooth, rugose. Color: Young foliage upper side: Near RHS Greyed-purple 187A and Greyed-purple N187A, colors present individually. Young foliage under side: Near RHS Greyed-green 197A and Greyed-purple 187A, colors present individually. Mature foliage upper side: Near RHS Green 137B. Mature foliage under side: Near RHS Greyed-Green 191A. Venation: Pattern: Pinnate-netted. Color upper side: Near RHS Yellow-Green 146D. Color under side: Near RHS Yellow-Green 146D. Fall foliage upper side: Near RHS Greyed-Purple 187B, 187C and N187A. Colors mottled together. Fall foliage under side: Near RHS Greyed-Purple 187B, 187C and N187A. Colors mottled together. Petiole: Average Length: Approximately 2.6 mm. Diameter: About 1 mm. Petiole color upper side: Near RHS Yellow-green 146D. Petiole color lower side: Near RHS Yellow-green 146D. Petiole Texture upper side: Smooth. Petiole Texture lower side: Smooth.

Flower:

*Natural flowering season*.—Late Spring to early Summer.

*Inflorescence type and habit*.—Single rotate flowers located on flattened terminal corymbs.

*Flower arrangement*.—Single rotate flowers.

*Quantity of flowers per inflorescence*.—Average 190.

*Inflorescence size*.—Width: Approximately 6.0 cm. Height: Approximately 1.8 cm.

*Quantity of flowers per lateral stem*.—190.

*Quantity of flowers and buds per plant*.—About 4,000.

*Individual flowers*.—Flower form: Rotate star shape. Flower aspect: Upright and outward. Flowering habit: Terminal. Size: Diameter: Approximately 6 mm. Length: Approximately 6 mm. Depth: Approximately 3 mm.

*Flower other characteristics*.—Persistence: Self cleaning. Fragrance: None.

*Petal*.—Petal arrangement: Single whorl of five petals, not fused. Petal appearance: Silky. Number of petals per flower: 5. Petal Shape: Widely obovate. Petal Base: Acute. Margin: Entire. Tip shape: Obtuse. Length: 2.2 mm. Width: 2 mm. Texture: Upper: Smooth. Lower: Smooth.

*Petal color*.—When opening: Upper surface: Near RHS Red-Purple 64B. Lower surface: Near RHS Red-Purple 64B. Fully opened: Upper surface: Near RHS Red-Purple 64B. Lower surface: Near RHS Red-Purple 67B. Fading: Upper surface: Near RHS Purple-Violet N80B. Lower surface: Near RHS Purple-Violet N80C.

*Bud*.—Shape: Orbicular. Length: Approximately 1.9 mm. Diameter: Approximately 1.75 mm. Color: Near RHS Greyed-purple N187A and Red-purple 64B, colors individually present.

*Sepals*.—Shape: Wide deltate. Arrangement: Single whorl of 5 sepals, fused into hypanthium. Number of Sepals: 5. Length: Approximately 1 mm. Width: Approximately 0.5 mm. Margin: Entire. Base: Truncate/fused. Tip: Cuspidate. Texture: Smooth all surfaces. Color: Upper side: Near RHS Greyed-Purple 186A. Lower side: Near RHS Green 138A.

*Calyx*.—Shape: Star shaped. Length: 4 mm. Diameter: 4 mm.

*Peduncle*.—Length: 3.6 cm. Diameter: 0.5 mm. Color: Near RHS Greyed-Green 195A. Orientation: 0-70°. Strength: Good. Texture: Smooth.

*Pedicel*.—Length: 1 mm. Diameter: about 0.5 mm. Color: Near RHS Greyed-Green 195A. Orientation: 30-60°. Strength: Moderately strong. Texture: Smooth.

Reproductive organs:

*Stamens*.—Number: Approximately 15. Filament length: 3.5 mm. Filament color: Near RHS Red-Purple N57B.

*Anthers*.—Shape: Elliptic. Length: less than 0.5 mm. Color: Near RHS Violet-Blue N92C. Pollen quantity: Moderate. Pollen Color: Near RHS Greyed-White 156A.

*Pistil*.—Number: 1. Length: About 2 mm. Style: Length: Approximately 1 mm. Color: Near RHS Red-Purple 60B. Stigma: Shape: Irregular retuse. Color: Near RHS Red-Purple 67A. Ovary color: Near RHS Yellow-Green 144C.

Other characteristics:

*Seeds and fruits*.—Moderate amount of minute, dust-like seeds enclosed in circular seed heads. Seed heads approximately 2 mm in diameter, colored near Brown 200B.

*Garden performance*.—Good performance in a garden setting, including tolerance for rain and wind.

*Disease/pest resistance*.—Neither resistance nor susceptibility to normal diseases and pests of *Spiraea* have been observed.

*Temperature tolerance*.—The new variety tolerates temperatures between −31° C. to 38° C.

What is claimed is:

1. A new and distinct cultivar of *Spiraea* plant named 'SMSJMLA' as herein illustrated and described.

* * * * *